United States Patent
Heuer et al.

(10) Patent No.: US 7,307,070 B2
(45) Date of Patent: Dec. 11, 2007

(54) MICROBICIDAL COMPOSITIONS

(75) Inventors: Lutz Heuer, Krefeld (DE); Peter Wachtler, Köln (DE); Michael Schwamborn, Köln (DE); Martin Kugler, Leichlingen (DE); Hans-Ulrich Buschhaus, Krefeld (DE)

(73) Assignee: Lanxess Deutschland GmbH, Leverkusen (DE)

( * ) Notice: Subject to any disclaimer, the term of this patent is extended or adjusted under 35 U.S.C. 154(b) by 892 days.

(21) Appl. No.: 09/901,979

(22) Filed: Jul. 10, 2001

(65) Prior Publication Data

US 2002/0004517 A1  Jan. 10, 2002

Related U.S. Application Data

(60) Division of application No. 08/888,609, filed on Jul. 7, 1997, which is a continuation of application No. 08/542,566, filed on Oct. 13, 1995, now abandoned, which is a continuation of application No. 08/338,356, filed on Nov. 14, 1994, now abandoned, which is a continuation of application No. 08/128,450, filed on Sep. 28, 1993, now abandoned.

(30) Foreign Application Priority Data

Oct. 5, 1992 (DE) .................... 42 33 337

(51) Int. Cl.
| | |
|---|---|
| A01N 55/00 | (2006.01) |
| A01N 43/64 | (2006.01) |
| A01N 43/36 | (2006.01) |
| A61K 31/40 | (2006.01) |

(52) U.S. Cl. .......................... 514/63; 514/383; 514/423
(58) Field of Classification Search .................. 514/63, 514/383, 423
See application file for complete search history.

(56) References Cited

U.S. PATENT DOCUMENTS

| | | | | |
|---|---|---|---|---|
| 4,664,696 A | * | 5/1987 | Schaub .......................... 71/92 |
| 4,849,439 A | | 7/1989 | Schaub ........................ 514/383 |
| 4,897,427 A | * | 1/1990 | Barnavon et al. ........... 514/383 |
| 4,994,480 A | | 2/1991 | Büchel et al. ............... 514/383 |
| 5,156,673 A | | 10/1992 | Metzner et al. .......... 106/15.05 |
| 5,200,421 A | | 4/1993 | Ludwig et al. ............. 514/383 |
| 5,223,524 A | * | 6/1993 | Valcke ........................ 514/383 |
| 5,248,450 A | | 9/1993 | Metzner et al. ............. 252/380 |
| 5,260,326 A | | 11/1993 | Sauter et al. ................ 514/383 |
| 5,373,013 A | * | 12/1994 | Hubele et al. ............... 514/275 |
| 5,373,934 A | | 12/1994 | Jackson et al. .......... 198/803.8 |
| 5,407,934 A | | 4/1995 | Küng ....................... 514/239.5 |

FOREIGN PATENT DOCUMENTS

| | | |
|---|---|---|
| EP | 050738 | 9/1981 |
| EP | 4 139 09 | 6/1990 |
| EP | 0393746 | 10/1990 |
| EP | 393746 | * 10/1990 |
| EP | 478195 | 4/1992 |
| EP | 0 554 833 | 2/1993 |
| EP | 0 555 186 | 2/1993 |
| NL | 8 701 282 | 1/1988 |

OTHER PUBLICATIONS

Worthing et al, "The Pesticide Manual", 9th Ed. (1991) pp. 86, 215, 216, 277, 420, 654, 701, 702, 724, 725, 785, 831, 832, 833+834.*
The Agrochemical Handbook, Royal Society of Chemistry, 3rd edition 1991.*
Proceedings-British Crop Protection Conference—Pest and Diseases, pp. 857-864 (1986).
English Abstract of EP 50738, Sep. 19, 1991.
English Abstract of EP 413909, Jun. 5, 1990.
English Abstract of WO 94/05636, Mar. 17, 1994.
Abstract of NL 8,701,282, Jan. 4, 1988.

* cited by examiner

*Primary Examiner*—Alton Pryor
(74) *Attorney, Agent, or Firm*—Norris McLaughlin & Marcus PA

(57) ABSTRACT

There are described the use of α-(4-chlorophenyl)-α-(1-cyclopropylethyl)-1H-1,2,4-triazole-1-ethanol as a microbicide for the protection of industrial materials, and compositions containing this compound.

3 Claims, No Drawings

MICROBICIDAL COMPOSITIONS

This application is a division of U.S. Ser. No. 08/888,609, filed on Jul. 7, 1997, now pending, which is, in turn, a continuation of U.S. Ser. No. 08/542,566, filed on Oct. 13, 1995, now abandoned, which is, in turn, a continuation of U.S. Ser. No. 08/338,356, filed on Nov. 14, 1994, now abandoned, which is, in turn, a continuation of U.S. Ser. No. 08/128,450, filed on Sep. 28, 1993, now abandoned.

The invention relates to the use of the compound α-(4-chlorophenyl-α-(1-cyclopropyl-ethyl)-1H-1,2,4-triazole-1-ethanol (cyproconazole) as a microbicide for the protection of industrial materials, and to synergistic mixtures containing this compound.

It has been disclosed that the azole derivatives described in DE-OS (German Published Specification) 3,406,993 can be used for protecting plants.

The present invention relates to the use of an azole derivative of the formula (I)

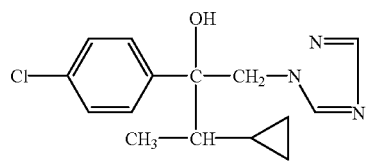

its metal salts or acid addition compounds as a microbicide for the protection of industrial materials.

The azole derivate can not only be in the form of the free base but also in the form of a metal salt complex or an acid addition salt. Suitable metal salts are preferably salts of metals of main groups II to IV and sub-groups I and II as well as IV to VII of the periodic table, the following being mentioned by way of example: copper, zinc, manganese, magnesium, tin, iron, calcium, aluminium, lead, chromium, cobalt and nickel.

Suitable anions of the salts are those which are derived, preferably, from the following acids: hydrohalic acids such as, for example, hydrochloric acid and hydrobromic acid, furthermore phosphoric acid, nitric acid and sulphuric acid.

The metal salt complexes of the azole derivative can be obtained in a simple manner by customary processes, for example by dissolving the metal salt in alcohol, for example ethanol, and adding the solution to the azole fungicide. Metal salt complexes can be isolated in a known manner, for example by filtration, and, if appropriate, purified by recrystallisation.

The following acids are preferably suitable for preparing acid addition salts of the azole derivative: the hydrohalic acids, such as, for example, hydrochloric acid and hydrobromic acid, in particular hydrochloric acid, furthermore phosphoric acid, nitric acid, sulphuric acid, mono- and bifunctional carboxylic acids and hydroxycarboxylic acids such as, for example, acetic acid, propionic acid, 2-ethylhexanoic acid, butyric acid, mandelic acid, oxalic acid, succinic acid, 2-hydroxy-ethane-dicarboxylic acid, maleic acid, fumaric acid, tartaric acid, citric acid, salicylic acid, sorbic acid, lactic acid, as well as sulphonic acids, such as, for example, p-toluenesulphonic acid, p-decyl phenyl sulphonic acid, p-dodecyl phenyl sulphonic acid, 1,4-naphthalenedisulphonic acid, alkanesulphonic acids, benzoic acid and optionally substituted benzoic acids.

The acid addition salts of the compounds can be obtained in a simple manner by customary salt formation methods, for example by dissolving a compound in a suitable inert solvent and adding the acid, for example hydrochloric acid, and they can be isolated in a known manner, for example by filtration, and, if appropriate, purified by washing with an inert organic solvent.

The compound (R*, R*)-α-(4-chlorophenyl-α-(1-cyclopropyl-ethyl)-1H-1,2,4-triazole-1-ethanol (cyproconazole) is particularly preferred.

Surprisingly, these compounds display a particularly powerful microbicidal, in particular fungicidal, activity against microorganisms which are relevant in the protection of materials, combined with a broad spectrum of action; they are active, above all, against molds and wood-discoloring and wood-destroying fungi. The following groups of microorganisms may be mentioned by way of example, but without imposing any limitation:

A: Wood-discoloring fungi:
  A1: Ascomycetes;
    *Ceratocystis* such as *Ceratocystis minor*
  A2: Deuteromycetes;
    *Aspergillus* such as *Aspergillus niger*
    *Aureobasidium* such as *Aureobasidium pullulans*
    *Dactylium* such as *Dactylium fusarioides*
    *Penicillium* such as *Penicillium brevicaule* or *Penicillium variabile*
    *Sclerophoma* such as *Sclerophoma pithyophila*
    *Scopularia* such as *Scopularia phycomyces*
    *Trichoderma* such as *Trichoderma viride* or *Trichoderma lignorum*
  A3: Zygomycetes:
    *Mucor* such as *Mucor spinorus*

B: Wood-destroying fungi:
  B1: Ascomycetes:
    *Chaetomium* such as *Chaetomium globosum* or *Chaetomium alba-arenulum*
    *Humicola* such as *Humicola grisea*
    *Petriella* such as *Petriella setifera*
    *Trichurus* such as *Trichurus spiralis*
  B2: Basidiomycetes
    *Coniophora* such as *Coniophora puteana*
    *Coriolus* such as *Coriolus versicolor*
    *Donkioporia* such as *Donkioporia expansa*
    *Glenospora* such as *Glenospora graphii*
    *Gloeophyllum* such as *Gloeophyllum abietinum* or *Gloeophyllum adoratum* or *Gl. protactum* or *Gloeophyllum sepiarium* or *Gl. trabeum*
    *Lentinus* such as *Lentinus cyathiformes* or *Lentinus edodes* or *Lentinus lepideus* or *Lentinus grinus* or *L. squarrolosus*
    *Paxillus* such as *Paxillus panuoides*
    *Pleurotus* such as *Pleurotis ostreatus*
    *Poria* such as *Poria monticola* or *Poria placenta* or *Poria vaillantii* or *Poria vaporaria*
    *Serpula* such as *Serpula himantoides* or *Serpula lacrymans*
    *Stereum* such as *Stereum hirsutum*
    *Tyromyces* such as *Tyromyces palustris*
  B3: Deuteromycetes
    *Alternaria* such as *Alternaria tenius*
    *Cladosporium* such as *Cladosporium herbarum*

The amount of active substance employed depends on the species and the occurance of the microorganisms, the microbial count and the medium. The optimum dosage rate for use can be determined in each case by test series. In general, however, it suffices to employ 0.001 to 20% by weight, preferably 0.05 to 10% by weight, of the active compound based on the material to be protected.

The active compound can be used as such, in the form of concentrates or generally customary formulations such as powder, granules, solutions, suspensions, emulsions or pastes.

The abovementioned formulations can be prepared in a manner known per se, for example by mixing the active compound with at least one solvent or diluent, emulsifier, dispersant and/or binder or fixative, water repellant, optionally siccatives and UV stabilisers, and optionally colorants and pigments as well as other processing auxiliaries.

Suitable solvents or diluents are organochemical solvents or solvent mixtures and/or a polar organic solvent or solvent mixture and/or an oily or oil-type organochemical solvent or solvent mixture and/or water, if appropriate together with an emulsifier and/or wetting composition. Customary water-insoluble oily or oil-type solvents of low volatility which are preferably used are the particular mineral oils/mineral-oil-containing solvent mixtures or their aromatic fractions. White spirit, petroleum or alkylbenzenes, and additionally spindle oil and monochloronaphthalene may be mentioned as being preferred. The boiling ranges of these solvent (mixtures) of low volatility cover a range of approximately 170° C. to not more than 350° C.

The above-described oily or oil-type solvents of low volatility can be replaced partially by more volatile organochemical solvents.

To prepare a wood preservative, some of the above described solvent or solvent mixture is preferably replaced by a polar organochemical solvent or solvent mixture. Solvents which are preferably used are those containing hydroxyl groups, ester groups, ether groups or mixtures of this functionality. Examples which may be mentioned are esters or glycol ethers. Binders are to be understood according to the invention as being synthetic resins, binding drying oils, for example based on acrylic resins, vinyl resins, polyester resins, polyurethane resins, alkyd resins, phenol resins, hydrocarbon resins or silicone resins which can be diluted with water or are soluble, dispersible or emulsifiable in organochemical solvents. The binder used can be employed as a solution, emulsion or dispersion. Mixtures of alkyd resins and drying vegetable oil are preferably used. Alkyd resins with an oil content of between 45 and 70% are particularly preferred.

All or some of the abovementioned binder can be replaced by a fixative (mixture) or a plasticiser (mixture). These additives are intended to prevent volitilisation of the active compound as well as crystallisation or precipitation. They preferably replace 0.01 to 30% of the binder (based on 100% of the binder used).

The plasticisers are from the chemical classes of the phthalic esters such as dibutyl, dioctyl or benzyl butyl phthalate, phosphoric esters such as tributyl phosphate, adipic esters such as di-(2-ethylhexyl) adipate, stearates such as butyl stearate and amyl stearate, oleates such as butyl oleate, gylcerol ethers or higher-molecular-weight glycol ethers, glycerol esters as well as p-toluenesulphonic esters.

Fixatives are based, from the chemical point of view, on polyvinyl alkyl ethers such as, for example, polyvinyl methyl ether, or ketones such as benzophenone or ethylenebenzophenone.

The preferred solvent or diluent is water, if appropriate in a mixture with one or more of the abovementioned solvents or diluents, emulsifiers and dispersants.

Industrial materials according to the invention are non-live materials which have been prepared for use in industry. For example, industrial materials which are intended to be protected by the active compound from microbial change or destruction can be glues, sizes, paper and board, textiles, leather, wood, paints and plastic articles, cooling lubricants and other materials which can be infested with, or decomposed by, micro-organisms. Parts of production plants, for example cooling-water circuits, which may be impaired by the multiplication of microorganisms may also be mentioned from amongst the materials to be protected. Preferred industrial materials beyond the scope of the invention are glues, sizes, paper and board, leather, wood, derived timber products, paints, cooling lubricants, aqueous hydraulic fluids and cooling circuits.

The active compound of the formula (I), or compositions or concentrates containing it, are preferably employed for protecting wood and derived timber products against microorganisms, for example against wood-destroying or wood-discoloring fungi, in particular in the protection of tropical wood.

Wood which can be protected by the active compound of the formula (I) or by mixtures containing them is to be understood as meaning, for example, structural timber, wooden beams, railway sleepers, components of bridges, jetties, vehicles made of wood, boxes, pallets, containers, telegraph poles, wooden fences, wooden lagging, windows and doors made of wood, plywood, chipboard, joinery, or wooden products which are used, quite generally, for building houses or in building joinery.

The protection of wood is particularly effective when large-scale impregnating treatments, for example vacuum, double vacuum or pressure treatments, are used.

The active compound of the formula (I) is preferably mixed with at least one other antimicrobially active substance, fungicide and, in particular, with other active compounds, to increase the spectrum of action or to achieve particular effects such as, for example, an additional protection against insects. In many cases, this results in synergistic effect, that is to say, the activity of the mixture is greater than the activity of the individual components. Particularly preferred components for the mixtures are, for example, the following compounds:

Sulphenamides, such as dichlofluanid, tolylfluanid, folpet and fluorfolpet;

Benzimidazoles, such as carbedazim, benomyl, fuberidazole, thiabendazole or their salts;

Thiocyanataes such as thiocyanatomethylthiobenzothiazole or methylene bis-thiocyanate;

Quarternary ammonium compounds such as benzyldimethyltetradecylammonium chloride, benzyldimethyldodecylammonium chloride or didecyldimethylammonium chloride;

Morpholine derivatives such as tridemorph, fenpropiomorph or falimorph;

Azoles such as triadimefon, triadimenol, bitertanol, tebuconazole, propioconazole, azaconazole, hexaconazole, prochloraz or bromuconazole, metconazole, penconazole, difenoconazole, fenbuconazole, opus, fensilazole.

2-(2-Chlorocyclopropyl)-1-(2-chlorophenyl)-3-(1,2,4-triazol-1-yl)-propan-2-ol;

Iodine derivatives such as diiodomethyl-p-tolyl sulphone, 3-iodo-2-propinyl alcohol, 4-chlorophenyl-3-iodopropargyl formal, 3-bromo-2,3-diiodo-2-propenyl ethylcarbonate, 2,3, 3-triiodoallyl alcohol, 3-bromo-2,3-diiodo-2-propenyl alcohol, 3-iodo-2-propinyl-n-butyl carbamate, 3-iodo-2-propinyl n-hexylcarbarnate, 3-iodo-2-propinyl cyclohexylcarbamate and 3-iodo-2-propinyl phenylcarbamate; O-1-(6-Iodo-3-oxo-hex-5-myl)butylcarbamate, O-1-(6-Iodo-3-oxo-hex-5-inyl)phenylcarbamate, Nepcodide VP 305.

Phenol derivatives such as derivatives such as tribromophenol, tetrachlorophenol, 3-methyl-4-chlorophenol, dichlorophen, o-phenylphenol, m-phenylphenol, p-phenylphenol or 2-benzyl-4-chlorophenol;

Bromine derivatives such as 2-bromo-2-nitro-1,3-propanediol or 2-Brom-2-brommethyl-glutaridinitril;

Isothiazolinones such as N-methylisothiazolin-3-one, 5-chloro-N-methyl-isothiazolin-3-one, 4,5-dichloro-N-octylisothiazolin-3-one or N-octyl-isothiazolin-3-one;

Benzoisothiazolinones or 4-5-trismethylen-N-methyl-isothiazol-3-on;

Pyridines such as 1-hydroxy-2-pyridinethione (and their sodium, iron, manganese and zinc salts) or tetrachloro-4-methylsulphonylpyridine;

Metal soaps such as tin naphthenate, tin octoate, tin 2-ethylhexanoate, tin oleate, tin phosphate, tin benzoate, copper naphthenate, copper octoate, copper 2-ethyl-hexanoate, copper oleate, copper phosphate, copper benzoate, zinc naphthenate, zinc octoate, zinc 2-ethylhexanoate, zinc oleate, zinc phosphate or zinc benzoate;

Oxides such as tributyltin oxide, $Cu_2O$, CuO or ZnO;

Dialkyldithiocarbamataes such as sodium and zinc salts of dialkylthiocarbamataes, tetramethylthiuram disulphide;

Nitriles such as 2,4,5,6-tetrachloroisophthalodinitrile;

Benzothiazoles such as 2-mercaptobenzothiazol;

Quinolines, such as 8-hydroxyquinoline, and their copper salts;

Boron compounds, such as boric acid, boric esters or borax;

Formaldehyde and formaldehyde-releasing compounds such as benzyl alcohol mono(poly)-hemiformal, oxazolidines, hexahydro-S-triazines, N-methylolchloroacetamide or paraformaldehyde;

Tris-N-(cyclohexyldiazeniumdioxy)-aluminium, N-(cyclohexyldiazeniumdioxy)-tributyltin or potassium salts thereof, or bis-N-(cyclohexyldiazeniumdioxy)-copper.

The following are preferably added as insecticide:

Phosphoric esters such as azinphos-ethyl, azinphos-methyl, 1-(4-chlorophenyl)-4-(O-ethyl, S-propyl)phosphoryloxypyrazole, chloropyrifos, coumaphos, demeton, demeton-S-methyl, diazinon, dichlorvos, dimethoate, ethoprophos, etrimfos, fenitrothion, fenthion, heptenophos, parathion, parathion-methyl, phosalone, phoxim, pirimiphos-ethyl, pirimiphos-methyl, profenofos, prothiofos, sulfprofos, triazophos and trichlorophon;

Carbamates such as aldicarb, bendiocarb, 2-(1-methyl-propyl)-phenyl methylcarbamate, butocarboxim, butoxycarboxim, carbaryl, carbofuran, carbosulfan, cloethocarb, isoprocarb, methomyl, oxamyl, pirimicarb, promecarb, propoxur and thiodicarb;

Organosilicon compounds, preferably dimethyl(phenyl)-silylmethyl 3-phenoybenzyl ethers, such as dimethyl-(4-ethoxyhpenyl)silylmethyl 3-phenoxybenzyl ether or (dimethylphenyl)-silyl-methyl 2-phenoxy-6-pyridylmethyl ethers such as, for example, dimethyl(9-ethoxy-phenyl)-silylmethyl 2-phenoxy-6-pyridylmethyl ether or [(phenyl)-3-(3-phenoxyphenyl)-propyl](dimethyl)-silanes, such as, for example, (4-ethoxyphenyl)-[3-(4-fluoro-3-phenoxy-phenyl-propyl]dimethyl silane.

Pyrethroids, such as allethrin, alphamethrin, bioresmethrin, byfenthrin, cycloprothrin, cyfluthrin, decamethrin, cyhalothrin, cypermethrin, deltamethrin, alpha-cyano-3-phenyl-2-methylbenzyl 2,2-dimethyl-3-(2-chloro-2-trifluoro-methylvinyl)cyclopropanecarboxylate, fenpropathrin, fenfluthrin, fenvalerate, flucythrinate, flumethrin, fluvalinate, permethrin, resmethrin and tralomethrin;

Nitroimines and nitromethylenes, such as 1-[(6-chloro-3-pyridinyl)-methyl]-4,5-dihydro-N-nitro-1H-imidazol-2-amine (imidacloprid).

The mixtures, concentrates and formulations according to the invention which have been prepared in this manner are not only active against the abovementioned fungi but also, if they contain an insecticide, against insects which destroy materials. The following insects which destroy materials may be mentioned by way of example, without imposing any limitation:

A: Dermaptera:
 Sirex juvencus
 Urocerus augur
 Urocerus gigas
 Urucerus gigas taignus B: Coleoptera:
 Anobium punctatum
 Apate monachus
 Bostrychus capucins
 Chlorophores pilosus
 Dendrobium pertinex
 Dinoderus minutus
 Ernobius mollis
 Heterobostrychus brunneus
 Hylotrupes bajulus
 Lyctus africanus
 Lyctus brunneus
 Lyctus linearis
 Lyctus planicollis
 Lyctus pubescens
 Minthea rugicollis
 Priobium carpini
 Ptilinus pecticornis
 Sinoxylon spec.
 Trogoxylon aequale
 Trypto dendron spec.
 Xestobium rufovillosum
 Xyleborus spec.

C: Isoptera:
 Coptotermes formosanus
 Cryptotermes brevis
 Heterotermes indicola
 Kalotermes flavicollis
 Mastotermes darwiniensis
 Reticulitermes flavipes
 Reticulitermes lucifugus
 Reticulitermes santonensis
 Zootermopsis nevadensis Other active compounds which are suitable are algicides, molluscicides or active compounds against sea animals which colonise, for example, ship's bottom paints.

The following are particularly preferred as components in mixtures:
 dichlofluanid, tolylfluanid,
 benzyldimethyldodecylammonium chloride, didecyldimethyl-ammonium chloride,
 tebuconazole, propiconazole, azaconazole, hexaconazole,
 3-bromo-2,3-diiodo-2-propenyl alcohol, 3-iodo-2-propinyl n-butylcarbamate,
 o-phenylphenol, m-phenylphenol, p-phenylphenol, 3-methyl-4-chlorophenol,
 thiocyanatomethylthiobenzothiazole, N-methylisothiazolin-3-one, 5-chloro-N-methylisothiazolin-3-one, 4,5-dichloro-N-octylisothiazolin-3-one, N-octyl-isothiazolin-3-one, benzyl alcohol mono(poly)-hemiformal, N-methylolchloroacetamide, phoxim, cyfluthrin, permethrin, cypermethrin, deltamethrin, imidacloprid.

The microbicidal compositions or concentrates used for the protection of industrial materials contain the active compound of the formula (I) in a concentration from 0.01 to 95% by weight, in particular 0.01 to 60% by weight, and additionally, if appropriate, 0.001 to 95% by weight of one or more other suitable fungicides, insecticides or other active compounds as mentioned above.

The compositions according to the invention allow in an advantageous manner the microbicidal compositions available to date to be replaced by more effective ones. They have good stability properties and, advantageously, a broad spectrum of action.

EXAMPLE 1

Inhibition test on giant colonies of Basidiomycetes

*Mycelium* sections were removed from colonies of *Gloeophyllum trabeum, Coniophora puteana, Poria* placenta, *Lentinus tigrinus, Coriolus versicolor* and *Stereum sanguinolentum* and incubated on an agar medium containing malt extract peptone at 26° C. The inhibition of hyphal growth on active-compound-containing media was compared with the longitudinal growth on media without an addition of active compound and rated as per cent inhibition.

At a concentration of 10 ppm, a 100% inhibition is obtained with the compound cyproconazole.

What is claimed is:

1. An antimicrobial composition comprising a synergistically effective amount therefor of:
    a) a first ingredient, which is α-(4-chlorophenyl)-α-(1-cyclopropylethyl)-1H-1,2,4-triazole-1-ethanol of the formula (I):

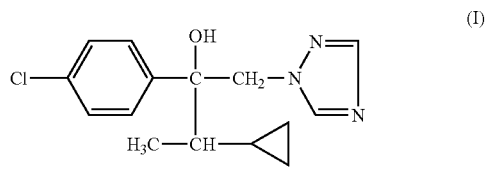

(cyproconazole) or a metal salt complex or acid addition salt thereof; and
   b) a second ingredient, which is an azole selected from the group consisting of tebuconazole and propiconazol.

2. A method of protecting an industrial material against the deleterious effects of microorganisms, said method comprising applying to said industrial material an amount of the antimicrobial composition according to claim 1 that is effective to protect said industrial material against said microorganisms.

3. The antimicrobial composition according to claim 1, wherein the second ingredient is tebuconazole.

* * * * *